US00PP32415P2

(12) United States Plant Patent
Olesen

(10) Patent No.: US PP32,415 P2
(45) Date of Patent: Nov. 3, 2020

(54) FLORIBUNDA ROSE PLANT NAMED 'POULCAS053'

(50) Latin Name: ***Rosa* hybrid**
Varietal Denomination: Poulcas053

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 16/602,262

(22) Filed: Sep. 3, 2019

(51) Int. Cl.
*A01H 5/02* (2018.01)
*A01H 6/74* (2018.01)

(52) U.S. Cl.
USPC ..... Plt./142
CPC ..... *A01H 6/749* (2018.05)

(58) Field of Classification Search
USPC ..... Plt./142
CPC ..... A01H 6/749; A01H 5/02
See application file for complete search history.

*Primary Examiner* — Keith O. Robinson

(57) ABSTRACT

A new garden rose plant of the Floribunda class which has abundant, red and pink striped flowers and attractive foliage. This new and distinct variety has shown to be uniform and stable in the resulting generations from asexual propagation.

2 Drawing Sheets

Botanical designation: *Rosa* hybrid.
Variety denomination: 'Poulcas053'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2010 and the resulting seeds were planted in a controlled environment in Fredensborg, Denmark. The new variety, named 'Poulcas053', originated as a single seedling from the stated cross.

The new variety may be distinguished from its male pollen parent and female seed parent primarily by the following characteristics. The male pollen parent plant has orange blend flowers while the new variety has red and pink striped flowers. The female seed parent plant has red flowers while the new variety has red and pink striped flowers.

The objective of the hybridization of this rose variety was to create a new and distinct variety with unique qualities, such as:

1. Uniform and abundant red and pink striped flowers;
2. Vigorous, but compact growth when propagated on its own roots;
3. Exceptional disease resistance.

This combination of qualities is not present in previously available commercial cultivars of this type, known to the inventor, and distinguish 'Poulcas053' from all other varieties of which we are aware.

As part of the rose development program, Mogens N. Olesen germinated the seeds from the aforementioned hybridization during winter of 2010 and conducted evaluations on the resulting seedlings in a controlled environment in Fredensborg, Denmark. 'Poulcas053' was selected in the spring of 2011 by the inventor as a single plant from the progeny of the aforementioned hybridization.

Asexual reproduction of 'Poulcas053' by rooted cuttings was first done by Mogens N. Olesen in the nursery in Fredensborg, Denmark in July, 2011. This initial and other subsequent asexual propagations conducted in controlled environments have demonstrated that the characteristics of 'Poulcas053' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulcas053'.

Specifically illustrated in FIG. 1 of the drawings are open flowers, petals and sepals detached showing reproductive flower parts, and flower buds.

Figure 1:
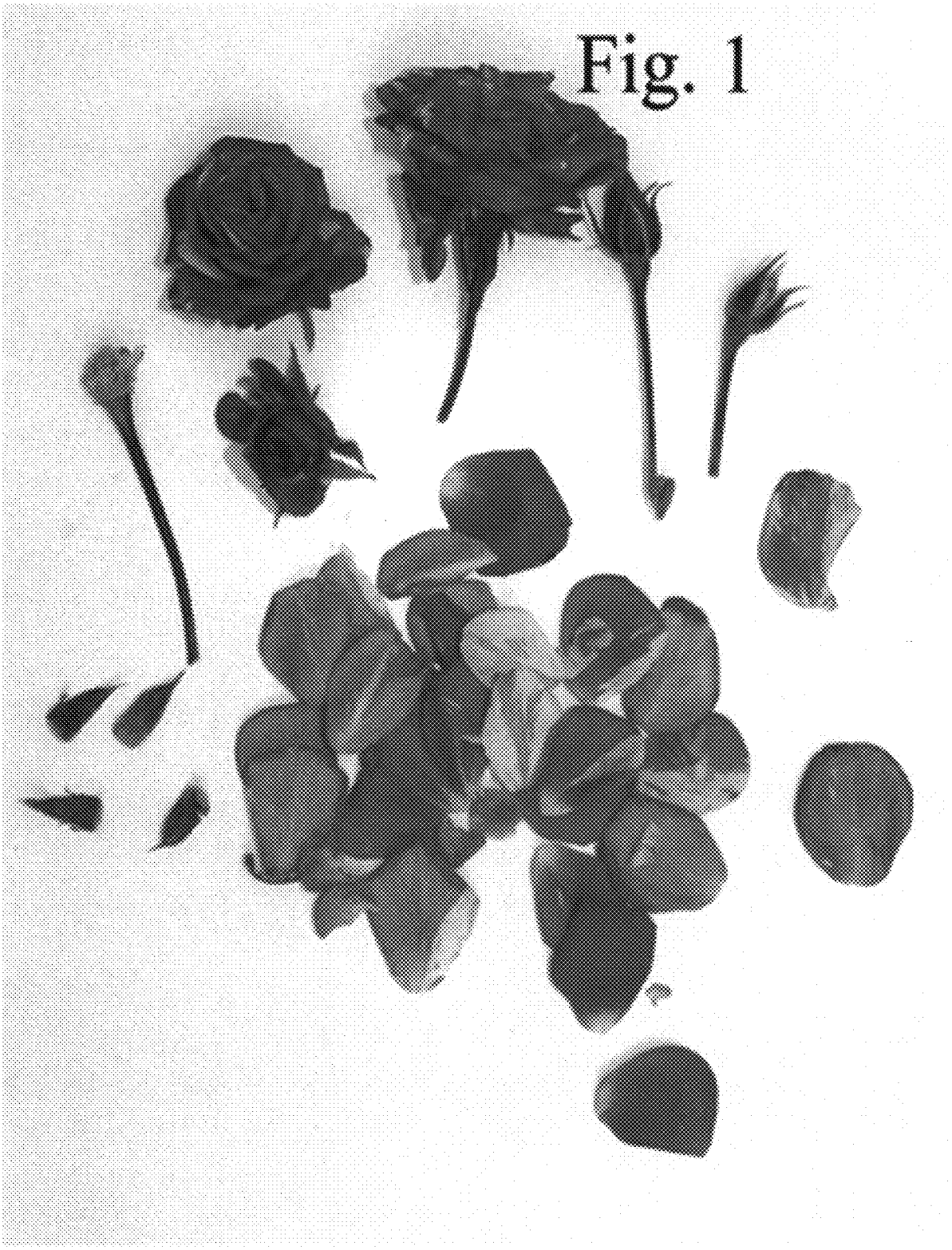
Figure 2:
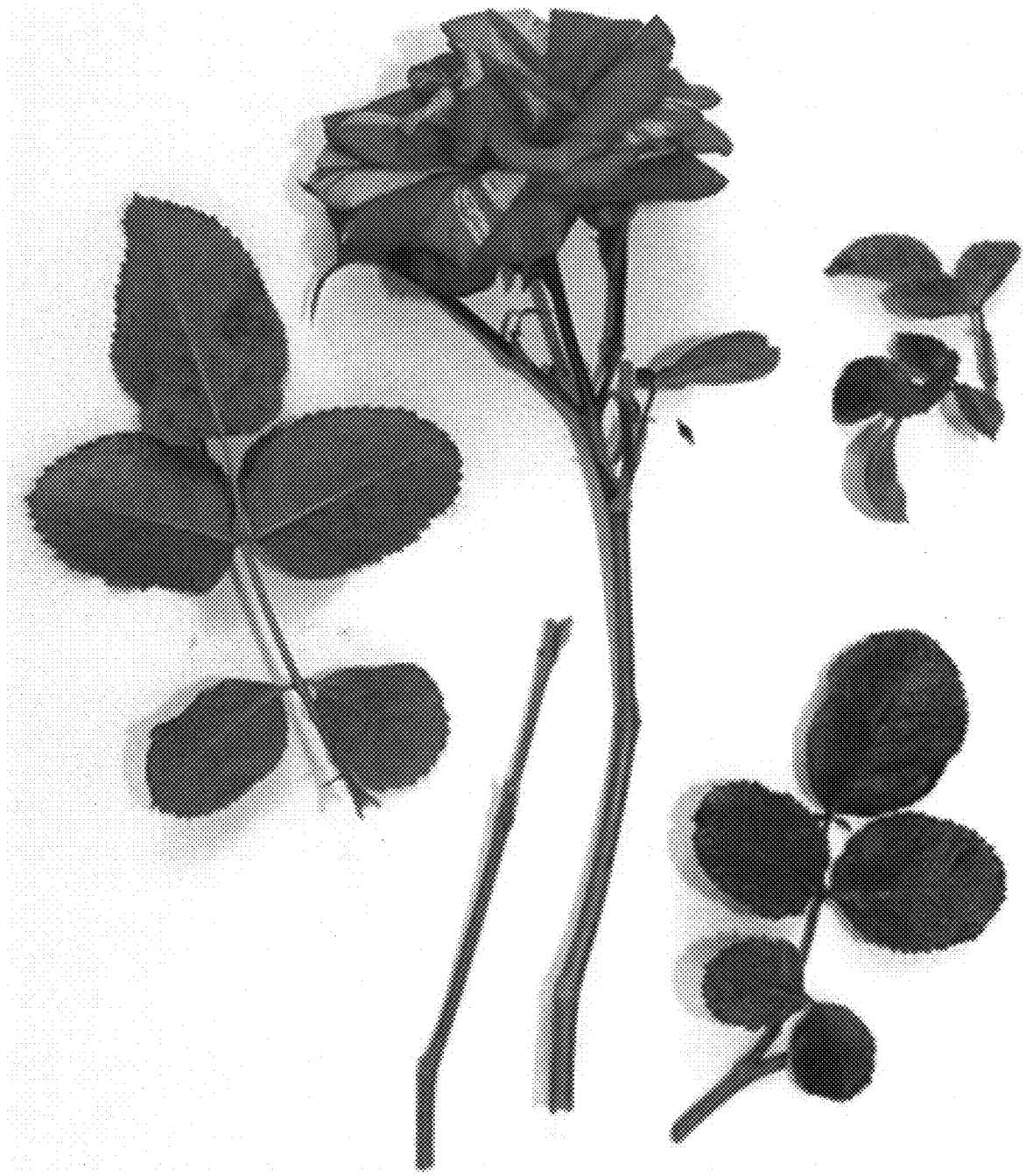

Specifically illustrated in FIG. 2 of the drawings are a cluster of open flowers on a branch, bare stem, juvenile and mature leaves. Plants shown are 2 years of age.

DETAILED DESCRIPTION OF THE VARIETY

The following is a description of 'Poulcas053', as observed in its growth in a field nursery in Linn County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulpah024', U.S. Plant Pat. No. 18,729 are compared to 'Poulcas053' in Chart 1.

CHART 1

| | 'Poulcas053' | 'Poulpah024' |
|---|---|---|
| Petal Count | 50 petals | 90 petals |
| Flower Diameter | 53 mm | 55 to 60 mm |
| Upper petal surface coloration, upon opening, outer petals | A blend of Red Group 53B and Red-Purple Group N57A splashed with Red-Purple Group 69B. | Steaks of Red-Purple 58B and Red Group 42A at the middle zone layered over yellow coloration which is Yellow Group 8D at the apex and Yellow Group 4B at middle zone. |

FLOWER AND FLOWER BUD

Blooming habit: Continuous.

Flower bud:

*Size.*—Upon opening, 25 mm in length from base of receptacle to end of bud. Bud diameter is 12 mm.

*Bud form.*—Ovoid.

*Sepal inner surface.*—Color: Yellow-Green Group 145A. Surface: Lightly pubescent.

*Sepal outer surface.*—Color: Yellow-Green Group 144A with intonations of Greyed-Red Group 178A. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—11 mm long, 6 mm wide.

*Receptacle.*—Texture: Smooth. Size: 5 mm in height, 5 mm wide. Color: Yellow-Green Group 144A with intonations of Greyed-Red Group 178A. Shape: Campanulate.

*Pedicel.*—Surface: Smooth. Length: 40 mm. Diameter: 1.5 mm on average. Color: Yellow-Green Group 144A with intonations of Greyed-Purple Group 183A. Strength: Strong.

*Peduncle.*—Length: 3 to 5 cm. Diameter: About 2.5 mm. Color: Yellow-Green Group 144A. Texture: Smooth.

Flower bud development: Flower buds are borne in clusters of 3 flower buds per stem on average.

Flower bloom:

*Fragrance.*—Moderate to strong, honey like perfume.

*Duration.*—The blooms have a duration on the plant of approximately 10 days. Petals fall cleanly away from plant after flowers have fully matured.

*Size.*—Flower diameter is 53 mm when open. Flower depth is 24 mm.

*Flower shape.*—High centered, double, with a high pointed center which is tightly closed.

*Shape of flower, side view.*—The upper portion is flat convex, and the lower portion is flat concave.

Petalage: Under normal conditions, flowers have about 50 petals.

General tonality of flower: Open flowers are Red-Purple Group N57A.

Petal color:

*Upon opening, and after opening outer petals.*—Upper surface: A blend of Red Group 53B and Red-Purple Group N57A splashed with Red-Purple Group 69B. Lower surface: Red-Purple Group 58B splashed with Red-Purple Group N57D.

*Upon opening, and after opening inner petals.*—Upper surface: Red Group 56C splashed with Red Group Purple Group N57B and Red-Purple Group N57C. Lower surface: Red-Purple Group N57A splashed with Red-Purple Group 60C. Basal petal spots, upon and after opening: Upper surface: Green Yellow Group 1D. Lower surface: Green Yellow Group 1D.

Petals:

*Petal reflex.*—Strong.

*Margin.*—Entire and uniform.

*Shape.*—Broad and elliptic. Apex shape: Rounded. Base shape: Acute.

*Size.*—32 mm (l)×33 mm (w).

*Texture.*—Smooth.

*Thickness.*—Average.

Petaloids:

*Size.*—9 mm (l) by 6 mm (w).

*Quantity.*—8 to 10.

*Shape.*—Irregular, with an acute base and rounded apices.

*Color.*—Upper surface is Red Group 56C splashed with Red Group Purple Group N57B and Red-Purple Group N57C. The lower surface is Red-Purple Group N57A splashed with Red-Purple Group 60C. At the base of the petaloid, Yellow Group 1D.

Reproductive flower parts:

*Pollen.*—None observed.

*Anthers.*—Size: 2 mm in length. Color: Yellow Group 8A. Quantity: 46 on average.

*Filaments.*—Color: White Group 155A. Length: 4 mm.

*Pistils.*—Length: 7 mm. Quantity: 30 on average.

*Stigmas.*—Color: Green Yellow 1D.

*Styles.*—Color: Green Yellow 1D.

*Location of stigmas.*—Superior in location relative to the length of the filaments and the height of the anthers.

*Hips.*—None Observed.

PLANT

Plant growth: Upright, bushy. Plants are 35 cm in height, and 40 cm wide.

Stems:

*Color of juvenile growth.*—Yellow-Green Group 144B.

*Color of mature growth.*—Yellow-Green Group 144A.

*Length.*—Canes are about 17 cm from the base of the plant to the flowering portion.

*Diameter.*—About 4 mm.

*Internodes.*—On mature canes about 45 mm between nodes.

*Surface texture.*—Young wood: Smooth. Older wood: Smooth.

Long prickles: None observed.

Plant foliage:

*Compound leaf.*—134 mm (l)×83 mm (w).

*Quantity.*—2 leaves per 10 cm of stem on average.

*Leaf bearing angle to the stem.*—45 degrees.

*Color of juvenile foliage.*—Upper side: Yellow-Green Group 144A. Lower side: Yellow-Green Group 144B.

*Color of mature foliage.*—Upper side: Yellow-Green Group 147B. Lower side: Yellow-Green Group 147C.

Plant leaves and leaflets:

*Stipules*.—Size: 15 mm long, 4 mm wide. Quantity: 2 per compound leaf. Shape: Linear, slightly broad based with outward extending apices. Margins: Finely serrated. Color: Yellow-Green Group 144A.

*Petiole*.—Length: 30 mm. Diameter: 1.5 mm. Upper surface color: Yellow-Green Group 144A. Lower surface color: Yellow-Green Group 144A.

*Rachis*.—Length: 50 mm. Upper surface color: Yellow-Green Group 144A. Lower surface color: Yellow-Green Group 144A.

*Leaflet*.—Quantity: Normally 5 leaflets. Margins: Serrated. Size: Terminal leaflets are about 55 mm long, 40 mm wide. Shape: Generally elliptical. Base: Rounded. Apex: Mucronate. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Floribunda rose class named 'Poulcas053', substantially as illustrated and described herein, due to its abundant red and pink striped flowers, disease resistance, and extended period of bloom.

* * * * *